United States Patent
Newby et al.

(10) Patent No.: US 9,701,939 B2
(45) Date of Patent: Jul. 11, 2017

(54) THERMORESPONSIVE CELL CULTURE SUPPORTS

(75) Inventors: Bi-Min Newby, Hudson, OH (US); Nikul Patel, Akron, OH (US); John Cavicchia, Libertyville, IL (US); Ge Zhang, Hudson, OH (US)

(73) Assignee: The University of Akron, Akron, OH (US)

( * ) Notice: Subject to any disclaimer, the term of this patent is extended or adjusted under 35 U.S.C. 154(b) by 187 days.

(21) Appl. No.: 14/110,465

(22) PCT Filed: Apr. 6, 2012

(86) PCT No.: PCT/US2012/032479
§ 371 (c)(1),
(2), (4) Date: Jan. 9, 2014

(87) PCT Pub. No.: WO2012/138968
PCT Pub. Date: Oct. 11, 2012

(65) Prior Publication Data
US 2014/0193911 A1    Jul. 10, 2014

Related U.S. Application Data

(60) Provisional application No. 61/473,318, filed on Apr. 8, 2011.

(51) Int. Cl.
*C12N 5/0775* (2010.01)
*C12N 5/00* (2006.01)

(52) U.S. Cl.
CPC ......... *C12N 5/0068* (2013.01); *C12N 5/0662* (2013.01); *C12N 5/0663* (2013.01); *C12N 5/0664* (2013.01); *C12N 5/0665* (2013.01); *C12N 5/0666* (2013.01); *C12N 5/0667* (2013.01); *C12N 5/0668* (2013.01); *C12N 2533/12* (2013.01); *C12N 2539/10* (2013.01)

(58) Field of Classification Search
CPC .............. C12N 5/0668; C12N 2533/12; C12N 2539/10
See application file for complete search history.

(56) References Cited

U.S. PATENT DOCUMENTS

| | | | |
|---|---|---|---|
| 2010/0216242 A1 | 8/2010 | Shimizu et al. | |
| 2012/0156781 A1 | 6/2012 | Takahashi et al. | |

OTHER PUBLICATIONS

Van den Brom, "The swelling behaviour of thermoresponsive hydrogel/silica nanoparticle composites" (Jan. 2010) Royal Society of Chemistry, vol. 20: 4827-4839.*
Yamada et al. "Thermo-responsive polymeric surfaces; control of attachment and detachment of cultured cells" (1990) Makromol. Chem. Rapid Commun., vol. 11: 571-576.*
Yakushiji et al. "Effects of Cross-Linked Structure on Temperature-Responsive Hydrophobic Interaction of Poly(N-isopropylacrylamide) Hyodrogel-Modified Surfaces with Steriods" (1999) Anal. Chem., vol. 71: 1125-1130.*
Fujita et al. "Application of a Cell Sheet-Polymer Film Complex with Temperature Sensitivity for Increased Mechanical Strength and Cell Alignment Capability" (2009) Biotechnology & Bioengineering, vol. 103, No. 2: 370-377.*
Moran, et al. "Cell growth and detachment from protein-coated PNIPAAm-based copolymers" J. Biomed. Mater. Res. 81, pp. 870-876 (2007).
Ward, et al. "Thermoresponsive Polymers for Biomedical Applications" Polymers 3, pp. 1215-1242 (2011).
Yamada, et al. "Thermoresponsive polymeric surfaces: control of attachment and detachment of cultured cells" Makromol. Chem. Rapid Comm. 11, pp. 571-576 (1990).
Nash, et al. "Straightforward, One-step Fabrication of Ultrathin Thermoresponsive Films from Commercially Available pNIPAm for Cell Culture and Recovery" ACS Appl. Mater. Interf. vol. 3, pp. 1980-1990 (2011).
Choi, et al. "Suppress Polystyrene Thin Film Dewetting by Modifying Substrate Surfaces with Aminopropyltriethoxylsilane" Surf. Sci. 600(6), pp. 1391-1404 (2006).
Caravaja, et al. "Structural characterization of (3-aminopropyl)triethoxysilane-modified silicas by silicon-29 and carbon-13 nuclear magnetic resonance" Anal. Chem. 60, pp. 1776-1786 (1988).
Vrancken, et al. "Surface modification of silica gels with aminoorganosilanes" Colloid Surf. A98, pp. 235-241 (1995).
Vihola, et al. "Cytotoxicity of thermosensitive polymers poly(N-isopropylacrylamide), poly(N-vinylcaprolactam) and amphiphilically modified poly(N-vinylcaprolactam)" Biomaterials 26, pp. 3055-3064 (2005).
Wadajkar, et al. "Cytotoxic evaluation of N-isopropylacrylamide monomoers and temperature-sensitive poly(N-isopropylacrylamide) nanoparticles" J. Nanopart. Res. 11, pp. 1375-1382 (2009).

* cited by examiner

*Primary Examiner* — Teresa E Knight
(74) *Attorney, Agent, or Firm* — Renner Kenner Greive Bobak Taylor & Weber

(57) ABSTRACT

The present invention relates to a cell culture support comprising a substrate and a thermoresponsive polymeric blend layer, wherein the polymeric blend layer comprises at least one thermoresponsive polymer and at least one network forming adhesion promoter. The present invention further relates a method of making a cell culture complex comprising: providing a substrate; blending at least one thermoresponsive polymer and at least one network forming adhesion promoter to provide a polymeric blend; applying a thin film of said polymeric blend to the substrate to provide a polymeric blend layer on the substrate; curing the polymeric blend layer on the substrate to provide a cell culture support; and depositing cells onto said cell culture support, wherein the cells may optionally further comprise medium, to provide a cell culture complex.

11 Claims, 5 Drawing Sheets

US 9,701,939 B2

THERMORESPONSIVE CELL CULTURE SUPPORTS

RELATED APPLICATIONS

This application claims the priority of provisional U.S. Application Ser. No. 61/473,318 filed Apr. 8, 2011.

TECHNICAL FIELD

The present invention relates to cell culture supports and methods of making cell culture supports. More particularly, this invention relates to thermoresponsive polymeric cell culture supports that are receptive to cell attachment and subsequent rapid cell sheet detachment. These supports are suitable for use, for example, in biomedical applications such as tissue engineering.

BACKGROUND OF THE INVENTION

Previous methods of preparing thermo-responsive cell culture supports have used two primary approaches, namely electron beam irradiation or plasma polymerization, to covalently graft poly (N-isopropylacrylamide) (pNIPAAm) chains onto tissue culture polystyrene dishes. The complicated procedures and apparatus required in these methods prevent a cost-effective adoption of this technology for specific applications. Furthermore, previous methods have generally required the use of added adhesive proteins from other individuals or other species to enhance cell attachment, and such foreign additions tend to cause immunogenic reactions of the cell sheet products after transplantation. Other methods that do not employ thermo-responsive polymers (TRPS) for detachment and harvesting of cell sheets from cell culture supports have employed proteolytic enzymes (e.g. trypsin) or mechanical agitations, which have resulted in damage to cells and their excreted extracellular matrix (ECM), thus negatively affecting their biological functions.

Nagase et al., as disclosed in J. R. Soc. Interface (2009) 6, S293-S309 and incorporated herein by reference, teach thermo-responsive micropatterned surfaces using electron beam polymerization techniques to allow the selective adhesion and growth of, for example, rat primary hepatocytes and bovine carotid endothelial cells. U.S. Pub. No. 2010/0216242 discloses a cell culture support including a polymer layer exhibiting thermoresponsiveness and a cell culture region obtained by plasma-treating a surface layer portion thereof with a reactive gas while limiting additions of cell adhesion proteins, such as collagen. However, these methods are still too expensive for wide-spread use.

Fujita et al., as disclosed in Biotechnology and Bioengineering, Vol. 103, No. 2, Jun. 1, 2009 and incorporated herein by reference, teach fabricating a cell sheet-polymer film complex involving a temperature-sensitive polymer in which cells are attached to a temperature-sensitive poly-N-isopropylacrylamide film mixed with laminin and collagen IV. As previously mentioned, added adhesive proteins are undesirable as they may deleteriously cause immunogenic reactions.

There is a need in the art for cell culture supports and methods of growing and releasing cell sheets therefrom that do not suffer from these various drawbacks. Also, the method should be simple and cost-effective to make it economically feasible for general biomedical applications.

SUMMARY OF THE INVENTION

The present invention provides a simple and cost effective approach to create thermoresponsive cell culture supports using commercially available materials. This is beneficially achieved without using expensive electron beam irradiation or plasma polymerization techniques. In addition, the present method is advantageously devoid of additional adhesive proteins and is further devoid of mechanical agitation or enzymatic aided detachment methods. The cell culture supports of the present invention employ a polymeric blend comprising a thermoresponsive polymer and a network forming adhesion promoter, wherein the network forming adhesion promoter enhances attachment and growth of cells on the cell culture support. It has been found that the cell culture supports of this invention support cell attachment and proliferation as well as rapid cell sheet detachment.

In a first embodiment, the present invention provides thermoresponsive cell culture supports that can be easily generated by spin-coating followed with a thermal annealing process; the resulting supports allow accelerated detachment of cells and confluent cell sheets; the resulting supports can be re-used (if needed) for up to three times for cell attachment/growth and detachment; the detachment times can be controlled by tailoring the ratios of the thermoresponsive polymer and the network forming adhesion promoter in the blend. The terms annealing and curing are used interchangeably herein.

In a second embodiment, the present invention provides a cell culture support comprising: a substrate and a polymeric blend layer bound to said substrate, wherein the polymeric blend layer comprises at least one thermoresponsive polymer and at least one network forming adhesion promoter.

In a third embodiment, the present invention provides a cell culture complex comprising: a substrate; a polymeric blend layer, wherein the polymeric blend layer comprises at least one thermoresponsive polymer and at least one network forming adhesion promoter; and a cultured cell layer, wherein the cultured cell layer is rapidly detachable.

In a fourth embodiment, the present invention provides a method of making a cell culture support comprising: providing a substrate; blending at least one thermoresponsive polymer and at least one network forming adhesion promoter to provide a polymeric blend; applying a thin film of said polymeric blend to the substrate to provide a polymeric blend layer on the substrate; and curing said polymeric blend layer on the substrate to provide a cell culture support.

In a fifth embodiment, the present invention provides a method of making a cell culture complex comprising: providing a substrate; blending at least one thermoresponsive polymer and at least one network forming adhesion promoter to provide a polymeric blend; applying a thin film of said polymeric blend to the substrate to provide a polymeric blend layer on the substrate; curing the polymeric blend layer on the substrate to provide a cell culture support; and depositing cells onto said cell culture support, wherein the cells may optionally further comprise medium, to provide a cell culture complex.

In a sixth embodiment, the present invention provides a method of making a cell sheet comprising: providing a substrate; blending at least one thermoresponsive polymer and at least one network forming adhesion promoter to provide a polymeric blend; applying a thin film of said polymeric blend to the substrate to provide a polymeric blend layer on the substrate; curing the polymeric blend layer on the substrate to provide a cell culture support; depositing cells onto said cell culture support, wherein the cells may optionally further comprise medium, to provide a cell culture complex; lowering the temperature of the cell culture complex to below the LCST to rapidly detach the cultured cell layer; and harvesting the cultured cell layer to provide a cell sheet.

In a seventh embodiment, the present invention provides a support, complex, or method as in any of the second through sixth embodiments, wherein the substrate is selected from the group consisting of polymeric materials, glasses, ceramics, metals, metal oxides, hydrated metal oxides, and combinations thereof.

In an eighth embodiment, the present invention provides a support, complex, or method as in any of the second through seventh embodiments, wherein the at least one thermoresponsive polymer is selected from the group consisting of poly (N-isopropylacrylamide) (PNIPAAm), poly(N,N-diethylacrylamide) (PDEAAm), poly(N-vinlycaprolactam) (PVCL), poly[2-(dimethylamino)ethyl methacrylate] (PD-MAEMA), and poly(ethylene oxide) (PEO), and combinations thereof.

In a ninth embodiment, the present invention provides a support, complex, or method as in any of the second through eighth embodiments, wherein the at least one thermoresponsive polymer is poly (N-isopropylacrylamide) represented by the formula:

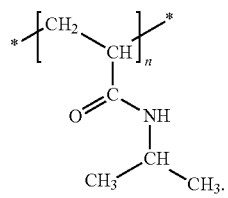

In a tenth embodiment, the present invention provides a support, complex, or method as in any of the second through ninth embodiments, wherein the at least one network forming adhesion promoter is characterized as having functional amino or carboxylic acid groups.

In an eleventh embodiment, the present invention provides a support, complex, or method as in any of the second through tenth embodiments, wherein the at least one network forming adhesion promoter is an aminosilane.

In a twelfth embodiment, the present invention provides a support, complex, or method as in any of the second through eleventh embodiments, wherein the at least one network forming adhesion promoter is selected from the group consisting of 3-aminopropyltriethoxysilane (APTES), 3-aminopropyldiethoxymethylsilane (APDEMS), and 3-aminopropyltrimethoxysilane (APTMS), and combinations thereof.

In a thirteenth embodiment, the present invention provides a support, complex, or method as in any of the second through twelfth embodiments, wherein the at least one network forming adhesion promoter is 3-aminopropyltriethoxysilane (APTES) represented by the formula:

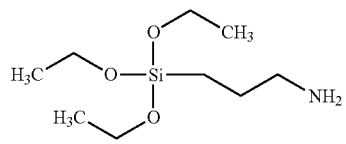

In a fourteenth embodiment, the present invention provides a support complex, or method as in any of the second through thirteenth embodiments, wherein the polymer blend is characterized as having a thermoresponsive polymer to network forming adhesion promoter ratio (TRP:NFAP) of from about 90:10 to about 40:60.

In a fifteenth embodiment, the present invention provides a support, complex, or method as in any of the second through fourteenth embodiments, wherein the cultured cell layer comprises cells further characterized as anchor dependent cells.

In a sixteenth embodiment, the present invention provides a support, complex, or method as in any of the second through fifteenth embodiments, wherein the cultured cell layer comprises cells further characterized as adhesive cells.

In a seventeenth embodiment, the present invention provides a support, complex, or method as in any of the second through sixteenth embodiments, wherein the cultured cell layer comprises cells selected from the group consisting of fibroblasts, myoblasts, myotube cells, corneal cells, vascular endothelial cells, smooth muscle cells, cardiomyocytes, dermal cells, epidermal cells, mucosal epithelial cells, mesenchymal stem cells, ES cells, iPS cells, osteoblasts, osteocytes, chondrocytes, fat cells, neurons, hair root cells, dental pulp stem cells, β-cells, hepatocytes, and combinations thereof.

In an eighteenth embodiment, the present invention provides a support, complex, or method as in any of the second through seventeenth embodiments, wherein the cultured cell layer comprises cells and medium.

In a nineteenth embodiment, the present invention provides a support, complex, or method as in any of the second through eighteenth embodiments, wherein the thin film of said polymeric blend is spin-coated onto the substrate.

In a twentieth embodiment, the present invention provides a support, complex, or method as in any of the second through nineteenth embodiments, wherein polymeric blend layer is substantially devoid of adhesive proteins.

In a twenty-first embodiment, the present invention provides a support, complex, or method as in any of the second through twentieth embodiments, wherein polymeric blend layer is substantially devoid of plasma or e-beam treatment.

In a twenty-second embodiment, the present invention provides a support, complex, or method as in any of the second through twenty-first embodiments, wherein the detachment of the cultured cell layer is substantially devoid of proteolytic enzymes or mechanical agitations.

DETAILED DESCRIPTION OF ILLUSTRATIVE EMBODIMENTS

Embodiments of the present invention are based upon the discovery of a cell culture support comprising a polymeric blend layer including a thermoresponsive polymer (TRP) and a network forming adhesion promoter whose molecules can form a crosslinked network using any type of annealing/curing processes. The polymeric blend layer is provided on an appropriate substrate, and the substrate and polymeric blend may be provided as a specific product for use in growing and harvesting cells. Advantageously, the cell culture support of certain embodiments provides for enhanced cell attachment (to create what is called herein a "cell sheet") and rapid subsequent cell sheet detachment, even though the cell culture supports are substantially devoid of proteins and enzymes previously employed to facilitate cell growth and harvest, respectively. Practice of the present invention has been found to be particularly useful in biomedical applications, such as tissue engineering, but it is also contemplated that the practice of this invention can be expanded to other applications in which cell culture supports are desired, such as in cell-based pharmaceutical studies and clinical therapeutics.

Figure 1A:
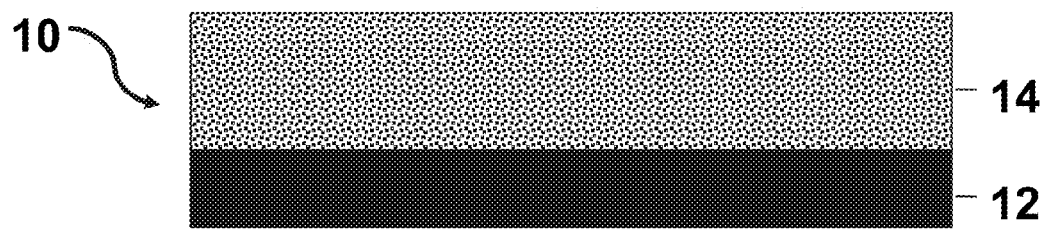
FIG. 1a illustrates an example of a cell culture support.

With reference to FIG. 1a, a cell culture support in accordance with this invention is shown and designated by the numeral 10. The cell culture support 10 includes a substrate 12 and a polymeric blend layer 14. The polymeric blend layer 14 is bounded to the substrate chemically by forming appropriate covalent bonds. For example, when organosilanes, such as aminopropertriethoxylsilane (APTES), are employed as the network forming adhesion promoter, the organosilanes are bonded to a substrate containing hydroxyl groups by forming siloxane bonds. Since APTES molecules also form a network by annealing, the polymer chains of the thermoresponsive polymer can be locked into the network, leading to the retention of the thermoresponsive polymer as well as the covalently bound network forming adhesion promoter on the substrate.

The substrate 12 can be provided in any useful form including, but not limited to, thin films, sheets, membranes, filters, nonwoven or woven fibers, hollow or solid beads, bottles, plates, tubes, rods, pipes, or wafers. The substrates can be porous or non-porous, rigid or flexible, transparent or opaque, clear or colored, and reflective or non-reflective. Suitable substrate materials are selected from the group consisting of polymeric materials, glasses, ceramics, metals, metal oxides, hydrated metal oxides, and combinations thereof.

Suitable glass and ceramic substrate materials include, for example, sodium, silicon, aluminum, lead, boron, phosphorous, zirconium, magnesium, calcium, arsenic; gallium, titanium, copper, and combinations thereof. Glasses typically include various types of silicate-containing materials.

In one or more embodiments, commercially available glass slides (Fisher Scientific, Waltham, Mass., USA) or P(100) test type silicon-wafers (Silicon Quest International, Santa Clara, Calif.) are useful in the practice of the present invention. Silicon wafers may also be referred to herein as Si-wafers.

In one or more embodiments of the present invention, the substrate may be tailored to any size and shape suitable in accordance with the requirements of the specific application. For example, the substrate dimensions may be tailored to the desired resultant cell sheet size. Typically, for the purposes of illustrating examples herein, glass slides and Si-wafers were cut into squares with a surface area of about 1 $cm^2$; however, the size of substrate contemplated may be virtually any size, and typically will range from about 0.01 to 100 $cm^2$.

The substrate is modified, if necessary, to provide functional groups at its surface suitable for covalently binding to the network forming adhesion promoter and/or thermoresponsive polymer of the polymeric blend layer 14. In the practice of a particular embodiment of the present invention, the substrate used contains hydroxyl groups (—OH) to allow the covalent bonding of APTES molecules to the substrate. Substrates containing amino (—$NH_2$) or carboxylic acid (—COOH) groups are also feasible.

Referring again to FIG. 1a, the cell culture support 10 of the present invention is comprised of a substrate 12 and a polymeric blend layer 14. The polymeric blend layer 14 comprises at least one thermoresponsive polymer (TRPs) and at least one network forming adhesion promoter. The TRP is desired because cell sheets formed on TRPs may be harvested (i.e., detached readily from the cell culture support) by a simple change of temperature, the temperature causing a spontaneous detachment of the cell sheet due to the change of the polymer chains from a hydrophobic to a hydrophilic nature. TRPs have the ability to respond to a change in temperature and can be classified into two main types: TRPs possessing a lower critical solution temperature (LCST) and TRPs possessing an upper critical solution temperature (UCST).

As will be described more particularly herein, the response of the TRP to temperature changes is advantageously employed to safely harvest cells sheets grown on the polymeric blend layer of the cell culture support 10. In the hydrophobic state, of the TRPs, the cell supports generally become more favorable for cells to attach and grow because of the exposed network forming adhesion promoter. As compared to the use of proteolytic enzymes (e.g. trypsin) or mechanical agitations to harvest cell sheets, using TRPs to harvest confluent cell sheets minimizes damage to cells and their excreted extracellular matrix (ECM), thus preserving their biological functions. Tissue engineering constructs based on cell sheets harvested according to the present invention allow increased cell-cell interactions and eliminate the risk of immunogenic materials present in scaffolds, the natural or synthetic biomaterials used in tissue engineering products to mimic ECM as a 3D cell culture environment. Furthermore, cell sheets harvested from TRPs can be patterned and assembled together to mimic the microarchitecture of native tissue, which is crucial for functional tissue regeneration.

The thermoresponsive polymer is not particularly limited herein, and a variety of publicly known polymers or copolymers can be used as the thermoresponsive polymer. These polymers can be crosslinked as needed, but only to an extent that their thermoresponsive properties are not lost. In one or more embodiments, the TRP is chosen to have a molecular chain length greater than its entanglement length.

In some embodiments, the TRP can be selected from virtually any TRP that becomes hydrophobic and undergoes chain collapsing at an elevated temperature that is generally above room temperature and preferably near the incubation temperature useful for growing the desired cells, and subsequently becomes hydrophilic and undergoes chain expansion at a decreased temperature that is generally lower than the elevated temperature. In one or more embodiments, the elevated temperature is preferably above room temperature.

In one or more embodiments, the decreased temperature is preferably near or below room temperature. Room temperature, or ambient temperature, is typically considered to be in the range from about 18° C. to about 25° C., more typically 20° C. to 23° C. In one or more embodiments, the decreased temperature is about room temperature.

In one or more embodiments, thermoresponsive polymers include various polyacrylamides, polyacrylamide derivatives and copolymers thereof.

In one or more embodiments, thermoresponsive polymers of the present invention are selected from the group consisting of poly-N-isopropylacrylamide (LCST=32° C.), poly-N-n-propylacrylamide (LCST=21° C.), poly-N-n-propylmethacrylamide (LCST=32° C.), poly-N-ethoxyethylacrylamide (LCST=~35° C.), poly-N-tetrahydrofurfurylacrylamide (LCST=~28° C.), poly-N-tetrahydrofurfurylmethacrylamide (LCST=~35° C.), poly-N,N-diethylacrylamide (LCST=32° C.), poly(C-isopropylacrylamide) (LCST=~32° C.) and combinations thereof (critical temperatures provided in parentheses).

In one or more other embodiments, the thermoresponsive polymers of the present invention are selected from the group consisting of poly-N-ethylacrylamide; poly-N-isopropylmethacrylamide; poly-N-cyclopropylacrylamide; poly-N-cyclopropylmethacrylamide; poly-N-acryloyl pyrrolidine; poly-N-acryloyl piperidine; polymethyl vinyl ether; alkyl-substituted cellulose derivatives such as methylcellulose, ethylcellulose, and hydroxypropylcellulose; polyalkylene oxide block copolymers typified by a block copolymer of polypropylene oxide and polyethylene oxide; and mixtures thereof.

In one or more embodiments of the present invention, suitable polymers with thermoresponsive properties are selected from the group consisting of poly (N-isopropylacrylamide) (pNIPAAm), poly(N,N-diethylacrylamide) (PDEAAm), poly(N-vinlycaprolactam) (PVCL), poly[2-(dimethylamino)ethyl methacrylate] (PDMAEMA), poly(ethylene oxide) (PEO), and combinations thereof. Poly (N-isopropylacrylamide), a commonly available TRP that presents an attractive lower critical solution temperature (LCST), may also be referred to interchangeably herein as poly-N-isopropylacrylamide, poly(N-isopropylacrylamide), PNIPAAm, pNIPA, pNIPAA, pNIPAm, or pNIPAAm.

PNIPAAm may be represented by the formula:

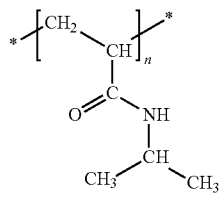

having both hydrophobic and hydrophilic groups, wherein the pNIPAAm chains collapse (lose H-bonds with $H_2O$ of the hydrophilic group) or extend (forms H-bonds with $H_2O$ of the hydrophilic group) depending on the temperature.

In one or more embodiments of the present invention, pNIPAAm (Sigma Aldrich, St. Louis, Mo., USA) is used as the thermoresponsive polymer. pNIPAAm is of special interest in bioengineering applications because of the phase change that it undergoes in a physiologically relevant temperature range. It has a lower critical solution temperature (LCST) of 32° C. in water. The polymer chains reside in a collapsed hydrophobic state above the LCST and in an extended hydrophilic state below LCST.

The polymeric blend layer 14 also includes a network forming adhesion promoter whose molecules can form a cross-linked network to lock in the TRP chains. The network formation should be achieved using a simple approach, e.g. thermo annealing at a temperature that causes no property change to the TRPs. By inter-locking TRP chains into the network, the chemical grafting of the TRP chains using facility intensive approaches, e.g. electron beam or plasma, is eliminated. In addition, the adhesion promoting properties of these molecules will enhance cell attachment and growth, circumventing the contamination issues of using adhesion proteins. The network forming adhesion promoters of the present invention are non-protein adhesion promoters.

In one or more embodiments, the network forming adhesion promoter of the present invention binds or attaches to the substrate. Without being bound by theory, attachment of the network forming adhesion promoter to the substrate is accomplished through covalent bonds, H-bonding, or other interactions including but not limited to van der Waals forces and other attachment/binding means as are known in the art could also be presented. The network forming adhesion promoter also acts to entangle or interlock the TRP chains and the network forming adhesion promoter provides protruding end groups for subsequent cell attachment.

In one or more embodiments, the network forming adhesion promoter may be characterized as having functional amino or carboxylic acid groups. Examples include but are not limited to aminosilanes, with primary or secondary amine functional groups.

In one or more embodiments, suitable network forming adhesion promoters are selected from the group consisting of 3-aminopropyltriethoxysilane (APTES),3-aminopropyldiethoxymethylsilane (APDEMS),3-aminopropyltrimethoxysilane (APTMS), 3-aminopropyltris(methoxyethoxyethoxy)silane (APTMEES), 4-aminobutyltriethoxysilane (ABTES), N-(2-aminoethyl)-3-aminoisobutylmethyldimethoxysilane (AEAIBMDMS), N-(2-aminoethyl)-3-aminopropylmethyldimethoxysilane (AEAPMDMS), N-(2-aminoethyl)-3-aminopropoysilanetriol (AEAPS), (aminoethylaminomethyl)phenethyltrimethoxysilane (AEAMPTMS), N-(2-aminoethyl)-3-aminopropyltriethoxysilane (AEAPTES), N-(2-aminoethyl)-3-aminopropyltrimethoxysilane (AEAPTMS), N-(6-aminohexyl)aminomethyltrimethoxysilane (AHAMTMS), N-(6-aminohexyl)aminopropyltrimethoxysilane (AHAPTMS), N-(2-aminoethyl)-11-aminoundecyltrimethoxysilane (AEAUDTMS),3-(m-aminophenoxy) propyltrimethoxysilane (APPTMS), m-aminophenyltrimethoxysilane (mAPTMS), p-aminophenyltrimethoxysilane (pAPTMS), aminophenyltrimethoxysilane (APTMS), N-[amino(polypropylenoxy)]aminopropyltrimethoxysilane (APEAPTMS),11-aminoundecyltriethoxysilane (AUDTS), and combinations thereof. The network forming adhesion promoter can also be selected from the group consisting of carboxyethlsilanetriol, 2(carbomethoxy)ethyltrichlorosilane, and 2-(carbomethoxy)ethylmethyldichlorosilane and combinations thereof. The network forming adhesion promoters used in the present invention generally include at least two head groups and an amino or carboxylic acid functional end group.

In one or more embodiments, the network forming adhesion promoter is 3-aminopropyltriethoxysilane (APTES) (Sigma Aldrich, St. Louis, Mo., USA). APTES is also referred to synonymously as 3-triethoxysilylpropylamine. APTES may be represented by the formula:

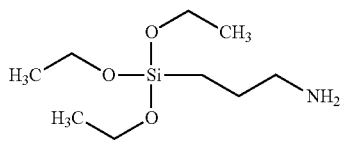

In one or more embodiments, the present invention is advantageously devoid of protein adhesion promoters, which are generally more complicated macromolecules and will not form the needed network to entrap TRP chains. Proteins as taught in the prior art are applied on top of the TRP layer, and are mainly adsorbed physically to the layer, thus they will most likely detach from the TRP layer and be retained with cells/cell sheets during harvesting. As such, these protein adhesives will be un-wanted foreign materials that cause contamination issues in the resulting cell sheets. In distinction, the network forming adhesion promoters used in the present invention will form a network and will be chemically anchored to the underneath substrate. Examples of unwanted proteins, of which the present invention is advantageously devoid of, include collagen, elastin, proteoglycans, glucosaminoglycans (hyaluronic acid, chondroitin sulfate, dermatan sulfate, heparan sulfate, heparin, keratin sulfate, etc.), fibronectin, laminin, hydronectin, gelatin, etc. in addition to RGD peptide, RGDS peptide, GRGD peptide, and GRGDS peptide.

In one or more embodiments of the present invention, the thermoresponsive polymer to network forming adhesion promoter ratio in the polymeric blend layer 14 is from about 99:1 to about 40:60, in other embodiments from about 95:5 to about 75:25, in other embodiments from about 95:5 to about 85:15, in yet other embodiments from about 88:12 to about 92:8, and in still other embodiments from about 89:11 to about 91:9. In a particular embodiment, the thermoresponsive polymer to network forming adhesion promoter ratio is 90:10. In one or more embodiments, the percentage of TRP in the polymer blend comprising TRP and network forming adhesion promoter, wherein the total of TRP and network forming adhesion promoter forms 100 weight percent (wt %), is at least 75 wt %, in other embodiments at least 80%, in other embodiment at least 85%, in other embodiment at least 86%, in other embodiment at least 87%, in other embodiment at least 88%, in other embodiment at least 89%, and in yet other embodiments at least 90%. In one or more embodiments, the percentage of TRP in the polymeric blend layer 14, wherein the total of TRP and network forming adhesion promoter is 100%, is at most 99 wt %, in other embodiments at most 98%, in other embodiment at most 95%, in other embodiment at most 94%, in other embodiment at most 93%, in other embodiment at most 92%, in other embodiment at most 91%, and in yet other embodiments at most 90%.

In particular embodiments employing pNIPAAm as the TRP and employing APTES as the network forming adhesion promoter, the above ratios are followed. In a particular embodiment, the polymeric blend layer 14 is a mixture of pNIPPAAm and APTES at a ratio of pNIPPAAm:APTES of from 40:60 to 90:10.

For silica based substrates (e.g. glass, Si-wafer), the substrates will be first appropriately cleaned. This may be achieved by application of a freshly prepared piranha solution (i.e. 70/30 v/v concentrated sulfuric acid/30% technical grade hydrogen peroxide) for 30-60 minutes, followed by a thorough rinsing with deionized water, and then oxidation using either UV/ozone or plasma (oxygen or air) for 5-10 minutes to generate the needed —OH groups on the surface. Other cleaning methods that will remove the organic contamination are also feasible. Metal substrates will be sonicated, in sequence, using water-immiscible organic solvent (i.e. toluene, hexane), followed with water-miscible organic solvents (e.g. acetone, ethanol) and finally water, for 5-10 minutes each, to remove contaminants. Then they will also be oxidized using either UV/ozone or plasma (oxygen or air) for 5-10 minutes to generate, for example, —OH groups. Other linkages besides —OH groups to provide polymer blend bonding onto the substrate are also contemplated, including but not limited to ester linkages for example. In one or more embodiments, the polymer substrates will be rinsed and sonicated with appropriate solvents and then coated with a thin layer of silica based materials via the sol-gel process to provide a silica surface that can be modified to provide —OH groups. In these embodiments, siloxane bonding is promoted whereby the head groups are hydrolyzed and converted to —OH groups providing stable linkages onto the substrate.

In one or more embodiments, the polymeric blend layer is applied to the substrate by first forming the polymeric blend of the TRP and the network forming adhesion promoter and then spin-coating, dip-coating or spreading the blend. The concentration of the solution can be tailored to achieve different film thickness. In one or more embodiments, the blended solution may comprise from about 0.5 to about 10 wt % total solute; in other embodiments from about 1 to about 5 wt % total solute; and in another embodiment from about 2 to 5 wt % total solute. In yet another embodiment, the concentration of the solute is about 3 wt %. In one or more embodiments, the polymeric blend is spin-coated to form a polymeric blend layer 14 on the substrate 12. Other techniques, as known in the art, may be used in addition to spin-coating including dip-coating and doctor blading.

The thickness of the polymeric blend layer may be variable and is not a critical parameter to the success of the cell culture support. Areas of excess thickness are not deleterious and will simply be washed away during preparation. In one or more embodiments, the thickness of the polymer layer is from about 15 nm to about 500 nm, in other embodiments from about 30 nm to about 400 nm, and in yet other embodiments from about 100 nm to about 200 nm. Generally, the thickness of the polymeric layer is greater than the thinnest layer (e.g. 8-10 nm) can be created by spin-coating of the interested polymer solution. In one or more embodiments, the thickness of the polymeric blend layer is at least 15 nm, in other embodiments at least 18 nm, in yet other embodiments at least 25 nm, and in still other embodiments at least 30 nm.

In one or more embodiments, after applying the polymeric blend of FIG. 1a to the substrate 12 and thereby forming the polymeric blend layer 14, the polymeric blend layer 14 is thermally annealed to allow the formation of the network and anchoring of the polymeric blend layer 14 to the substrate. While thermal annealing is the easiest approach to achieve the desired bonding/network formation, other methods, such as UV irradiation, could be applied. Annealing serves to bond the network forming adhesion promoter to the substrate and to form the network to lock the chains of the thermoresponsive polymer inside the network, intimately holding the polymeric blend layer 14 to the substrate 12. A suitable annealing temperature and time will be readily selected by those of skill in the art for a given polymeric blend layer 14 and substrate 12. The conditions (temperature, time) for annealing may vary depending upon the specific polymer blend type and ratio, but typically may range from about 80° C. to about 210° C. or higher for a time of about 24 hours to about 72 hours. In one or more embodiments, the polymer blend is annealed at a temperature from about 115° C. to about 205° C. for a time of about 24 hours to about 72 hours. In another embodiment, the polymer blend layer is annealed at about 160° C. for about 48 hours.

In a particular embodiment employing pNIPAAm and APTES, the APTES is cured by the application of heat, causing siloxane bonds to be formed. The pNIPAAm chains are interlocked in the APTES network as the network is being formed.

After the step of annealing the polymeric blend layer 14, the substrate 12 and annealed polymeric blend layer 14 is placed inside a cell incubation dish, and the temperature is brought above the LCST of the thermoresponsive polymer. This will cause the thermoresponsive polymer chains to collapse, exposing the cell adhesion functionality (e.g. amino group) of the network forming adhesion promoter. This exposing of the cell adhesion functionality facilitates subsequent cell attachment and growth of a cell sheet, and this exposure can be reversed by lowering the temperature to allow for a quick detachment of the cell sheet. This will be disclosed in more detail herein below.

In a particular embodiment employing pNIPAAm and APTES, the amino groups of the APTES molecules residing at the surface of the pNIPAAm/APTES network are exposed to the surrounding environment when the pNIPAAm chains collapse at a temperature greater than its LCST. Exposed amino groups promote cell attachment and proliferation.

Figure 1B:
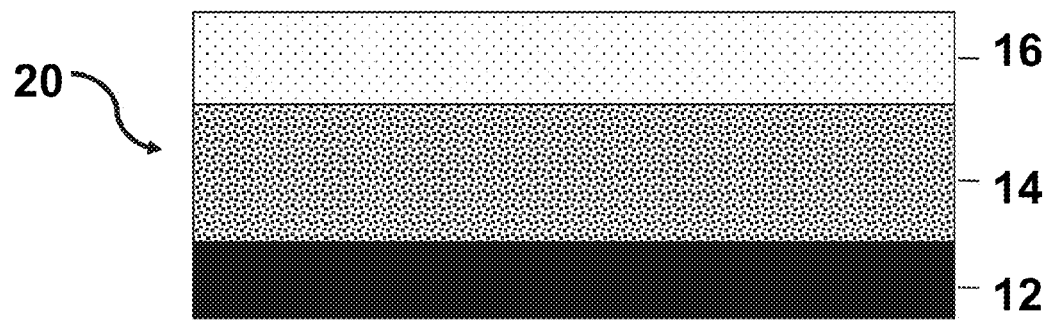
FIG. 1b illustrates an example of a cell culture complex.

The cell culture support 10 of the present invention, as shown in FIG. 1a, is useful for culturing anchor dependent cells. In one or more embodiments, the cultured cells are grown into cell sheets to provide, as schematically shown in FIG. 1b, a cell culture complex 20 with a cultured cell sheet 16 that can be subsequently harvested from the cell culture support by temperature induced (i.e. lowering the temperature) detachment. The detachment advantageously occurs rapidly. An advantage of the present invention is that the cell culture support 10 may be patterned and assembled together to mimic the microarchitecture of native tissue, which is crucial for functional tissue regeneration. Therefore the cultured cell layer 16 may take on any size and shape desired for various applications. The cells to be cultured in the cell culture complex 20 are not particularly limited herein so long as they are anchor dependent cells.

As used herein "anchor dependent cells" are to be understood as cells that grow, survive or maintain function only when attached to a surface.

Examples of anchor dependent cells, or alternatively referred to as adhesive cells, are selected from the group consisting of: fibroblasts, myoblasts, myotube cells, corneal cells, vascular endothelial cells, smooth muscle cells, cardiomyocytes, dermal cells, epidermal cells, mucosal epithelial cells, mesenchymal stem cells, ES cells, iPS cells, osteoblasts, osteocytes, chondrocytes, fat cells, neurons, hair root cells, dental pulp stem cells, β-cells, hepatocytes, and combinations thereof. In the description herein the term "cells" refers not only to individual cells, but also includes cells constituting tissues collected from the body.

When the use of these cells in regenerative medicine in humans and the like is taken into consideration, preferably, autologous cells will be used. Cells of heterozoic origin can be used as long as they provide acceptable immunocompatibility, and among allogeneic cells, either heterologous or autologous cells can be used.

In one or more embodiments of the present invention, human mesenchymal stem cells (hMSCs) (Lonza, Walkersville, Md.) are used. Tissue engineering constructs based on cell sheets of the present invention allow increased cell-cell interactions and eliminate the risk of immunogenic materials present in scaffolds.

After creation of the cell culture support 10 and the exposure of the cell adhesion functionality of the network forming adhesion promoter, cells are deposited onto the cured polymeric blend layer 14 and permitted to grow. In one or more embodiments, growth may occur, as is known in the art, in an incubator and/or in a nutrient bath. The cells are cultured by incubating in a warm (i.e. above LCST) medium according to normal specifications and then seeded onto the polymeric blend layer 14 with exposed cell adhesion functionality. After seeding, the cells are grown inside the incubator at 37° C. (>LCST) to confluence to form the cultured cell sheet 16 and provide the cell culture complex 20.

The conditions (temperature, time) for culturing depends upon the specific cells to be cultured, but typically may range from about 33° C. to about 38° C. for a time of about 6 hours to about 30 days. The present invention advantageously uses simple technology and is devoid of techniques utilizing brushes or proteins.

Subsequently upon cells growing to confluence and forming the cell sheet 16, lowering the temperature of the cell culture complex 20, and particularly the temperature of the thermoresponsive polymer of the polymeric blend layer, to a temperature that is less than the LCST of the thermoresponsive polymer, causes the chains of the thermoresponsive polymer to expand and cover the adhesion groups of the network forming adhesion promoter, thus preventing the interaction between the cell sheet 16 and the network forming adhesion promoter and allowing for quick and easy detachment of the cell sheet 16.

Figure 2A:
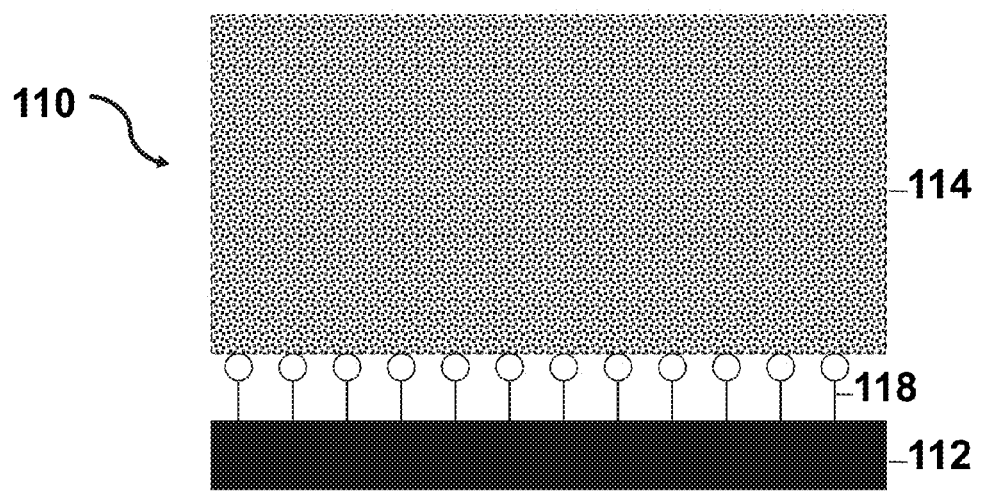
FIG. 2a schematically represents the application of a polymer blend of APTES molecules/pNIPAAm chains to a substrate.

Without intending to be bound to a specific theory, a particular embodiment is schematically depicted in FIG. 2a, b, c and d, with reference to a cell culture support 110 having a glass substrate 112 and a polymeric blend layer 114 of pNIPAAm (TRP) and APTES (network forming adhesion promoter). In FIG. 2a, the polymer blend 114 is applied to the substrate 112 which further includes substrate functional groups 118, which may be —OH groups.

Figure 2B:
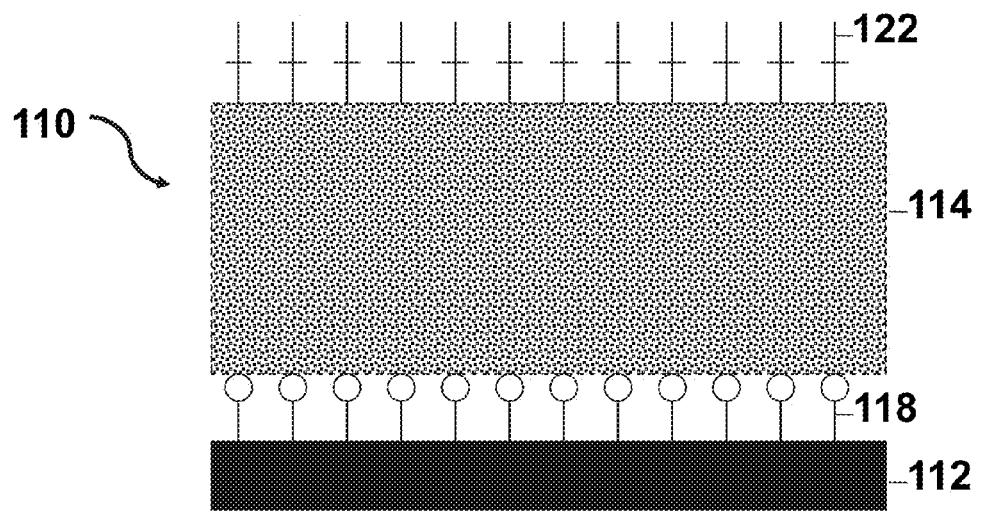
FIG. 2b schematically represents the thermal annealing of the polymer blend of FIG. 2a to cross-link the APTES network/pNIPAAm chains and to expose —NH$_2$ groups (from the APTES) at the surface to promote subsequent cell adhesion.

In FIG. 2b after thermal annealing of the polymer blend, polymer blend functional groups 122 are evident at the surface. Inter-penetrated pNIPAAm chains are locked inside the APTES network as siloxane bonds are being formed by curing, and at T>LCST, pNIPAAm chains collapsed to expose the —$NH_2$ groups of the APTES, thus enhancing cell attachment.

Figure 2C:
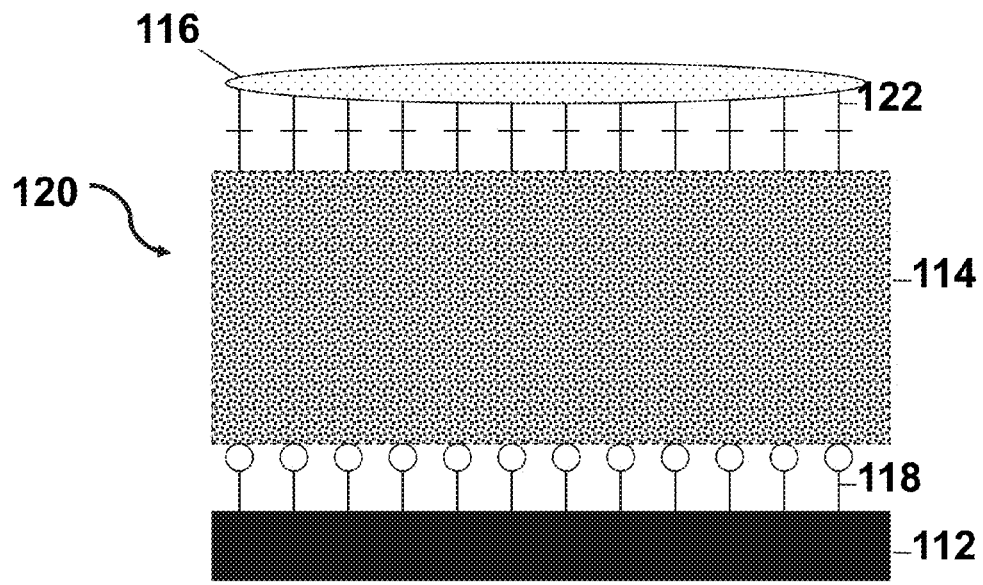
FIG. 2c schematically represents cell attachment and growth.
Figure 2D:
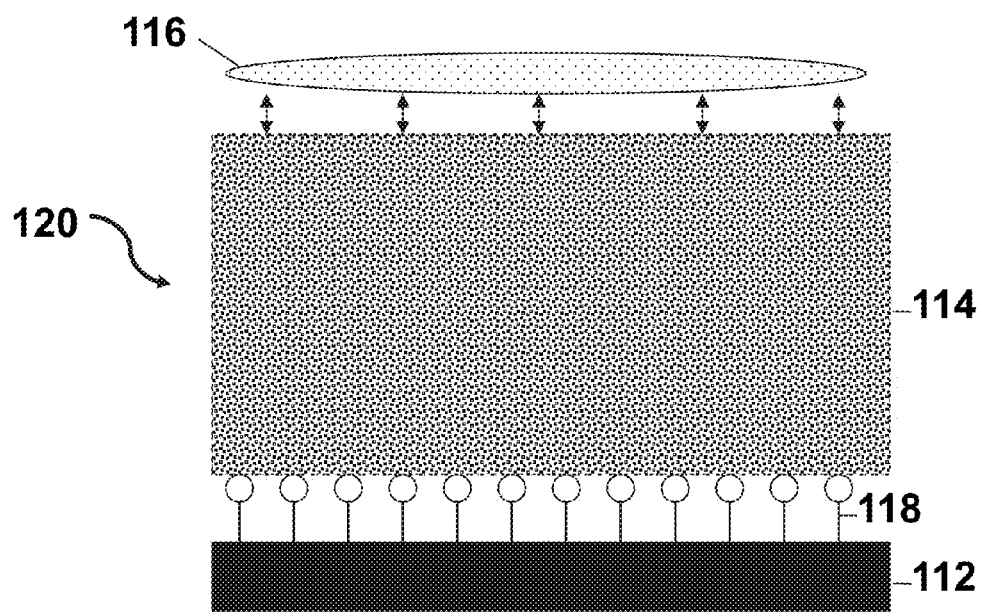
FIG. 2d schematically represents the hydrated pNIPAAm chains in the APTES network as temperature is lowered to below LCST; the expanded chains thus 'burying' the —NH$_2$ groups allowing for rapid cell detachment.

In FIG. 2c, cells 116 are applied and attached to the polymer blend functional groups 122 of the cell culture complex 120. After cell attachment and growth (to confluent), a lowering in temperature to T<LCST leads to pNIPAAm chain extension, and buries the —$NH_2$ groups of the APTES, thus allowing cell sheet 116 detachment as shown in FIG. 2d.

Lowering the temperature of the cell culture medium, or replacing it with fresh cold medium, hydrates the pNIPAAm chains and changes their conformation to the extended form. This phase change acts to bury the APTES surface amino groups and push the cell sheet away from the surface, allowing the detachment of the confluent sheet of cells. Furthermore, manipulating the amount of APTES blended in pNIPAAm/APTES films would control the cell sheet detachment rate, which could play a significant role in future tissue engineering applications.

The thermoresponsive polymer/network forming adhesion promoter blend, or more simply referred to as the polymer blend, of the present invention may be tailored to provide optimum cell attachment and, subsequently, rapid detachment for harvesting. Without being bound by theory, cell detachment is likely due to the extension of pNIPAAm chains burying the $NH_2$ groups of APTES, covering the anchor points needed for cell attachment. Increasing the amount of APTES in the pNIPAAm/APTES blend leads to an increased amount of anchor points for cell attachment; however, this leads to slower cell detachment upon cooling. For practical use, detachment times of less than 10 minutes are desired.

Referring again to FIG. 1a, the cell culture support 10 is comprised of a substrate 12 and a polymeric blend layer 14. Care in preparation of the substrates is taken to prevent contamination, which is important to the successful culturing of cells. The substrate 12 is first prepared to remove organic contaminants. This may be accomplished by immersing the substrates, such as non-limiting examples glass slides or silicon wafers, in a solution comprising 70 vol % $H_2SO_4$ and 30 vol % of 30% $H_2O_2$ or other suitable solution as is known in the art. The substrates are then rinsed with deionized water and dried with nitrogen gas followed by further cleaning in an UV/Ozone Cleaner for ten minutes.

In one or more embodiments of the present invention, a polymeric blend layer 14 may prepared as follows. Separately, a 3 wt % pNIPAAm solution in ethanol and a 10 wt % APTES solution in ethanol are prepared. The solutions are then blended in varying solution ratios of pNIPAAm: APTES. In one or more embodiments, the blended solution may comprise about 3 wt % total solute. Solutions are filtered, for example using a PTFE membrane, to remove particulates. Polymer blend films are produced by spin-coating, or other thin film technique as previously described and as are known in the art, onto the prepared substrates. In one or more embodiments of the invention, a thin film of thermoresponsive polymer/network forming adhesion promoter blend is spin-coated onto substrates for about 30 seconds at 2000 rpm to form a polymeric blend layer 14. The thickness of the polymeric blend layer typically ranges from about 200 nm to about 400 nm. The cell culture support 10 is then cured or annealed as previously described. In one or more embodiments, the cell culture supports are cured inside a vacuum for about one to three days at a temperature ranging from about 115° C. to about 205° C. to enable thermal annealing of the polymer blend network. After curing, the cell culture supports according to the present invention may be advantageously stored and/or transported for later use.

As shown in FIG. 1 b, the cell culture complex 20 is comprised of a substrate 12, a cured polymeric blend layer 14, and a cultured cell layer 16. In one or more embodiments of the invention, cells are deposited onto the cured cell culture supports. In one or more embodiments, the cultured cell layer 16 includes culture medium specific to the particular cells chosen for culturing according to application and use. After depositing onto the cell culture support, the cells are grown to confluence to form a cultured cell layer 16, which may also be referred to as a cell sheet, to provide a cell culture complex 20.

According to at least one embodiment of the present invention after cells are grown to confluence to form a cultured cell layer 16, the cell sheet may be rapidly detached from the cell culture complex 20 for use in a variety of applications. The cell culture complex of the present invention advantageously achieves detachment without using mechanical agitations or proteolytic enzymatic means to aid detachment. In one or more embodiments, detachment of the cultured cell layer 16 is induced by replacing the warm cell culture medium with fresh cold medium wherein the temperature is about 4° C. The cool medium acts to lower the temperature of the cell culture complex 20 below the LCST to provide for detachment of the cultured cell layer 16 within minutes. Alternatively in the absence of medium, other means of lowering the temperature of the cell culture complex below the LCST include refrigeration, soaking in cool water, or taking from warm place to room temperature, as well as other techniques as are known in the art.

In one or more embodiments of the present invention, the cell culture supports of the present invention may be used repeatedly. By using the supports more than once (typically supports may be used two to three times), the economic advantage of the present invention is yet furthered realized.

In order to demonstrate the practice of the present invention, the following examples have been prepared and tested. The examples should not, however, be viewed as limiting the scope of the invention. The claims will serve to define the invention.

EXAMPLE 1

Materials pNIPAAm, a molecular weight of 20-25 kg/mol, and 3-aminopropyltriethoxysilane (APTES) were purchased from Sigma Aldrich (St. Louis, Mo., USA). Glass slides and P(100) test type silicon-wafers were purchased from Fisher Scientific (Waltham, Mass., USA) and Silicon Quest International (Santa Clara, Calif.), respectively. All other chemical reagents were purchased from Sigma Aldrich unless otherwise indicated.

Preparation of Glass and Silicon Wafer (Si-Wafer) Substrates.

Glass slides and Si-wafers were cut into squares with a surface area of ~1 $cm^2$. Slides and wafers were immersed in freshly prepared piranha solution (70 vol. % of concentrated $H_2SO_4$ and 30 vol. % of 30% $H_2O_2$) for 1 hour at 100° C. to remove organic contaminants. After decanting the piranha solution, the slides were thoroughly rinsed with deionized (DI) water and dried with nitrogen ($N_2$) gas. Afterwards, the slides and/or wafers were oxidized in a UV/Ozone Cleaner (Jelight Company Inc, Irvine, Calif.) for 10 minutes for further cleaning.

Preparation of pNIPAAm/APTES Solutions.

A 3% wt. pNIPAAm solution and a 10% wt. APTES solution in ethanol (Pharmco-AAPER, Inc., Shelbyville, KT) were prepared separately. Solutions having pNIPAAm to APTES ratios (by mass) of 90:10, 80:20, 60:40, and 40:60 were prepared by mixing the proper ratios of the two above solutions and a small amount of ethanol to make a final solution containing ~3 wt. % of total solute. The solutions were subsequently filtered to remove particulates through an Acrodisc® CR 13 mm Syringe filter with a 0.45 µm PTFE membrane (Pall Life Sciences, Co., Ann Arbor, Mich.).

Preparation of pNIPAAm/APTES Films.

Polymer blend films were produced by spin coating the pNIPAAm/APTES mixed solution onto pre-cleaned substrates for 30 seconds at 2000 rpm (p-6000 Spin Coater, Specialty Coating Systems, Inc, Indianapolis, Ind.). The spin-coated samples were cured inside a vacuum (<100 mTorr) oven (VWR International, Radnor, Pa.) for 3 days at the following temperatures: 115° C., 145° C., 160° C., 175° C., and 205° C.

Water Contact Angles of pNIPAAm/APTES Thin Films.

The sessile drop method was utilized to measure the static water contact angles on the pNIPAAm/APTES films. Contact angles were recorded using a goniometer (Ramé-Hart Instrument Co, Netcong, N.J.) with a modified stage, which was heated to ~45° C. and then placed in a petri dish. The sample was positioned on top of the heated stage, and a drop of DI water was placed on the sample. The temperature of the stage was decreased continuously to ~25° C. by adding chilled water in the petri dish. As the temperature decreased, the sessile drop images of DI water on the sample were recorded using a Diamond VC500 one-touch video capture system (Diamond Multimedia, Chatsworth, Calif.) while the associated elapsed time was manually recorded. Still images were extracted out of the video clip and the contact angle was measured using ImageJ software (National Institutes of Health, Bethesda, Md.).

Thickness of pNIPAAm/APTES Films.

A manual photoelectric ellipsometer (Rudolph Instruments, Inc., Fairfield, N.J.) was used to measure the thicknesses of different pNIPAAm/APTES films on Si-wafers at a 632 nm wavelength. A refractive index of 1.48 for pNIPAAm was used for thickness calculations for the blended films, which might have a slightly different refractive index compared to a pure pNIPAAm film. Thickness measurements were taken of films made with different pNIPAAm/APTES ratios and/or cured at different temperatures. Samples were measured before and after immersion in cold DI water (immersed samples were dried by a stream of nitrogen before measurement). Two thickness measurements for each sample, and multiple samples (n=3) treated under the same condition were measured to provide the statistical values.

Diffuse Reflectance Infrared Fourier Transform (DRIFT) of pNIPAAm/APTES Films.

DRIFT spectra were obtained from films spin-coated on Si-wafers and cured under identical conditions as films on glass slides. A small sample, ~6 mm×6 mm in size, was placed at the center of the sample holder after ensuring the IR beam was properly focused on the sample. A small hemi-spherical dome (with a base diameter of ~2 cm) covered the sample. After securing the dome by fastening the screws, argon (Ar) gas was allowed to flow into the dome for ~5 minutes to replace the air inside and minimize water content. Then, a single beam spectrum was recorded using a Nicolet Magna 560 at 2 cm$^{-1}$ resolution using the Harrick Praying Mantis diffuse reflectance accessory at room temperature. Absorbance was obtained by Abs.=−log(I/I$_o$), where I and I$_o$ are the normalized intensities of the sample and of an oxidized Si-wafer (i.e. reference) respectively. The normalization was achieved by dividing the intensity at a particular wavelength by the maximum intensity of the spectrum. The maximum intensity for all the spectra obtained ranged from 1.60 to 1.79, depending on how the IR beam was focused on the sample surface. The normalization was applied to minimize the variation of the IR beam intensity used for scanning the samples under different scanning conditions and operated by different operators.

Cell Attachment.

Human mesenchymal stem cells (hMSCs) (Lonza, Walkersville, Md.) were cultured in serum-containing MSCBM medium (Lonza) supplemented with MSCGM SingleQuots (Lonza) according to manufacturer's specifications. To observe cell attachment, hMSCs (Passage 3) were seeded onto different substrates: a clean glass substrate, a pNIPAAm film, a 90:10 pNIPAAm/APTES film cured at 160° C., and a tissue culture polystyrene (TOPS) dish at a density of 1.5×10$^4$ cells/cm$^2$. Contrast phase pictures were taken 4 hours after cell seeding on each of the surfaces using an Axiovert 40 CFL (Carl Zeiss, Inc, Thornwood, N.Y.) microscope equipped with an AxioCam MRm camera (Carl Zeiss, Inc). A MTT cell proliferation assay (Invitrogen, Carlsbad, Calif.) was performed to compare the proliferative potential of cells on different substrates. The MTT solution absorbance was measured at a wavelength of 570 nm using a Synergy H1 Hybrid microplate reader (BioTek, Winooski, Vt.). For each group, 3 samples were tested.

Cell Sheet Detachment.

After the cells grew to confluence and formed a cell sheet on the pNIPAAm/APTES film, detachment was induced by replacing the warm cell culture medium with fresh cold medium (4° C.). Cells grown on UpCell® dishes were used for comparisons. An Observer Z1 Time lapse microscope (Carl Zeiss, Inc) was used to monitor and record cell detachment behavior. The cell images were taken every 10 seconds by an AxioCam MRm camera (Carl Zeiss, Inc) controlled by AxioVision (Carl Zeiss, Inc) software until the cell sheet was completely detached.

pNIPAAm/APTES Blend Films Support Cell Attachment and Proliferation.

hMSCs were seeded on different substrates and observed under a phase contrast microscope. After 4 hours of seeding, low hMSC attachment was observed on glass surfaces. hMSCs exhibited a rounded morphology and poor attachment on pNIPAAm only films cured at 160° C. for 3 days. Most of the hMSCs attached and spread on the 90:10 pNIPAAm/APTES films, also cured at 160° C. for 3 days, and on TCPS dishes. Cell proliferation was measured using the MTT assay. There was a significant increase in absorbance after 5 days for hMSCs on pNIPAAm/APTES films and the positive control (hMSCs on TCPS culture dish). The proliferation of hMSCs on the pNIPAAm/APTES films was comparable to proliferation on TCPS dishes after 5 days of seeding. A dip in absorbance was observed for the pNIPAAm only film, which may be due to the medium change performed at day 4. The pNIPAAm only films were not tightly bound to the underneath substrate and were easily rinsed away with the cells during medium change.

General Properties of pNIPAAm/APTES Films.

Prepared solutions were all transparent, indicating complete dissolution of the pNIPAAm/APTES mixture in ethanol. Films spin-coated on silicon wafers appeared to have a uniform color throughout the sample except at the edges where a slightly thicker film might result. There was a slight color change of each sample before and after curing, mainly from purplish/golden to mostly golden. Films cured at ~115° C. and 145° C. appeared to completely dissolve away when dipped into a bath of DI water at room temperature (~25° C. <LCST). Films cured at higher temperatures (160° C. to 205° C.) underwent a color change, but were still retained on the substrate.

The ellipsometry measurements, referring to Table 1, showed that upon dipping in a DI water bath at room temperature, a layer as thick as ~200-250 nm was removed from a ~300-350 nm pNIPAAm/APTES film cured at 160° C. and above. Thickness of films after dipping in room temperature cell culture medium was also measured and was found to be not significantly different from that of films after dipping in DI water. Repeated dipping of the films did not further reduce the film thickness. Prolonged (e.g. 3 days) immersion in room temperature water showed minimal reduction in thickness (~4%; data not shown). Films cured at temperatures of 145° C. and below showed that only a very thin layer (<10 nm) remained after dipping.

TABLE 1

Film thickness of pNIPAAm/APTES films prepared under different conditions and the cured films before and after dipping in DI water at room temperature.

| Sample Cured at 160° C. with different pNIPAAm/APTES ratios | | | Sample with the pNIPAAm/APTES ratio of 90/10 cured at different temperatures | | |
|---|---|---|---|---|---|
| | Thickness (nm) | | | Thickness (nm) | |
| pNIPAAm/APTES | Initial | Final | Temperature ° C. | Initial | Final |
| 90/10 | 353.1 ± 16.3 | 120.6 ± 3.8 | 115 | 396.1 ± 0.7 | 6.1 ± 0.2 |
| 80/20 | 377.4 ± 8.5 | 128.7 ± 11.6 | 145 | 378.3 ± 1.1 | 8.7 ± 2.3 |
| 70/30 | 389.3 ± 4.4 | 106.2 ± 3.3 | 160 | 353.1 ± 16.2 | 120.6 ± 3.8 |
| 60/40 | 409.1 ± 1.2 | 116.8 ± 25.3 | 175 | 293.9 ± 0.6 | 102.4 ± 1.2 |
| 50/50 | 343.1 ± 77.6 | 118.6 ± 0.7 | 205 | 322.6 ± 0.2 | 105.1 ± 0.6 |
| 40/60 | 379.8 ± 1.9 | 113.0 ± 0.8 | | | |

For pure pNIPAAm and pNIPAAm/APTES blended films, the infrared spectroscopy signature peaks of pNIPAAm (N—H at ~3300 $cm^{-1}$, C=O at ~1640 $cm^{-1}$, and the doublet for —HC(CH$_3$)$_2$ at ~1390 and ~1360 $cm^{-1}$) were observed. For blended films, the peaks of free APTES molecules (—OH stretching in ≡Si—OH at 3050-3700 $cm^{-1}$, 2880-2980 $cm^{-1}$ for —CH$_2$ stretching, 1475 $cm^{-1}$ for —CH$_2$ scissoring) were hard to distinguish since they overlapped with the —NH and —CH$_2$ peaks of pNIPAAm. The peak associated with cross-linked APTES molecules (≡Si—O—Si≡ stretching at 1050-1150 $cm^{-1}$) was observed for films cured for three days at a temperature of 160° C. or higher, but the peak intensity was relatively weak. For the high temperature cured films, the non-hydrogen bonded N—H stretching was also observed at 3442 $cm^{-1}$. After dipping in cool DI water, all peak intensities decreased while the signature peaks associated with pNIPAAm remained noticeable.

Water contact angles confirmed pNIPAAm/APTES films were thermo-responsive. The water contact angle decreased with a decrease in temperature, dropping from an angle of ~70° at a temperature of ~40° C. to about 30° at a temperature of ~26° C. In general, the contact angle change rapidly occurred in the temperature range of 31-34° C. for the pNIPAAm/APTES films cured at 160° C. or above for 3 days.

Figure 3:
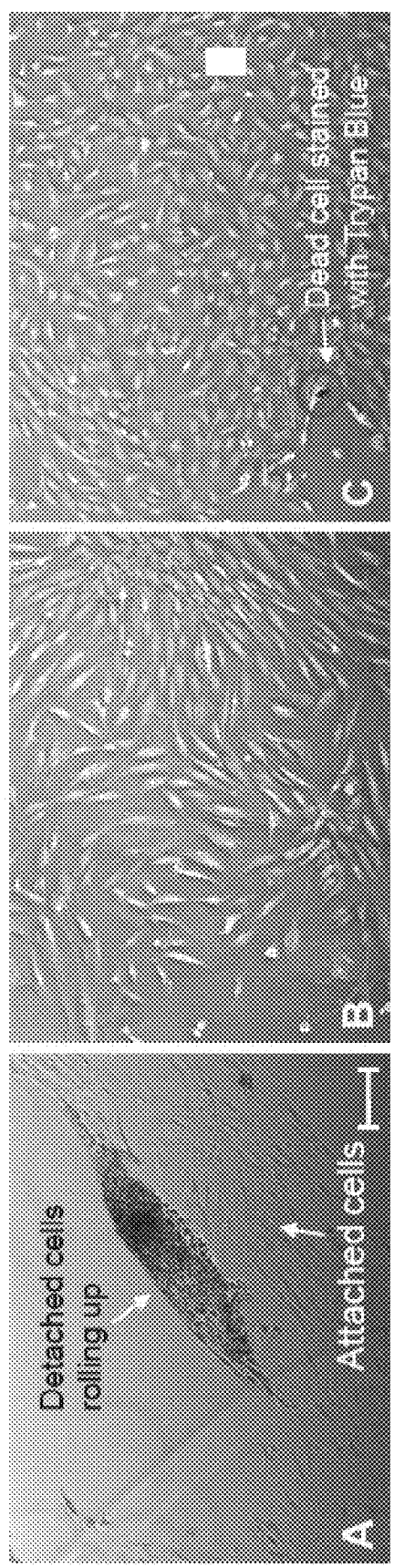
FIG. 3a-c include optical microscope (OM) phase-contrast images showing cell detachment behaviors.

Cell Detachment on pNIPAAm-APTES Films.

hMSCs were cultured on pNIPAAm/APTES films to assess individual cell and cell sheet detachment resulting from temperature change. Upon 80% confluence, cell detachment was achieved by replacing the cell culture medium with fresh cold medium (4° C.). The cell detachment behaviors are shown in FIG. 3a-c. Most cells returned to a round morphology as they lost their anchor points, while a few cells that had formed ECM connections remained bound together as shown in FIG. 3c. All cells detached within 2.5 minutes after adding cold medium (see the video clip in the supplemental data section). Under the same conditions, it took nearly 3 hours for the cells to completely detach from the commercial thermo-responsive cell culture surface (UpCell®).

The cell sheet detachment was assessed the same way as the aforementioned individual cell detachment. After adding cold medium, the confluent cell sheet detached from one end and rolled up (FIG. 3a). The entire detachment process took approximately 2.5 minutes from the point cold media was added to when all cells had detached from the 90:10 160° C. cured pNIPAAm/APTES film. Cell viability before and after detachment was also examined using trypan blue staining.

FIG. 3c shows minimal cell death after detachment from our surface, revealing that the detachment process does not harm the cells significantly. UpCell® surfaces were found to take ~11 hours for the cell sheet to completely detach when using the same protocols.

Cell Detachment as a Function of pNIPAAm-APTES Ratios.

Figure 4:
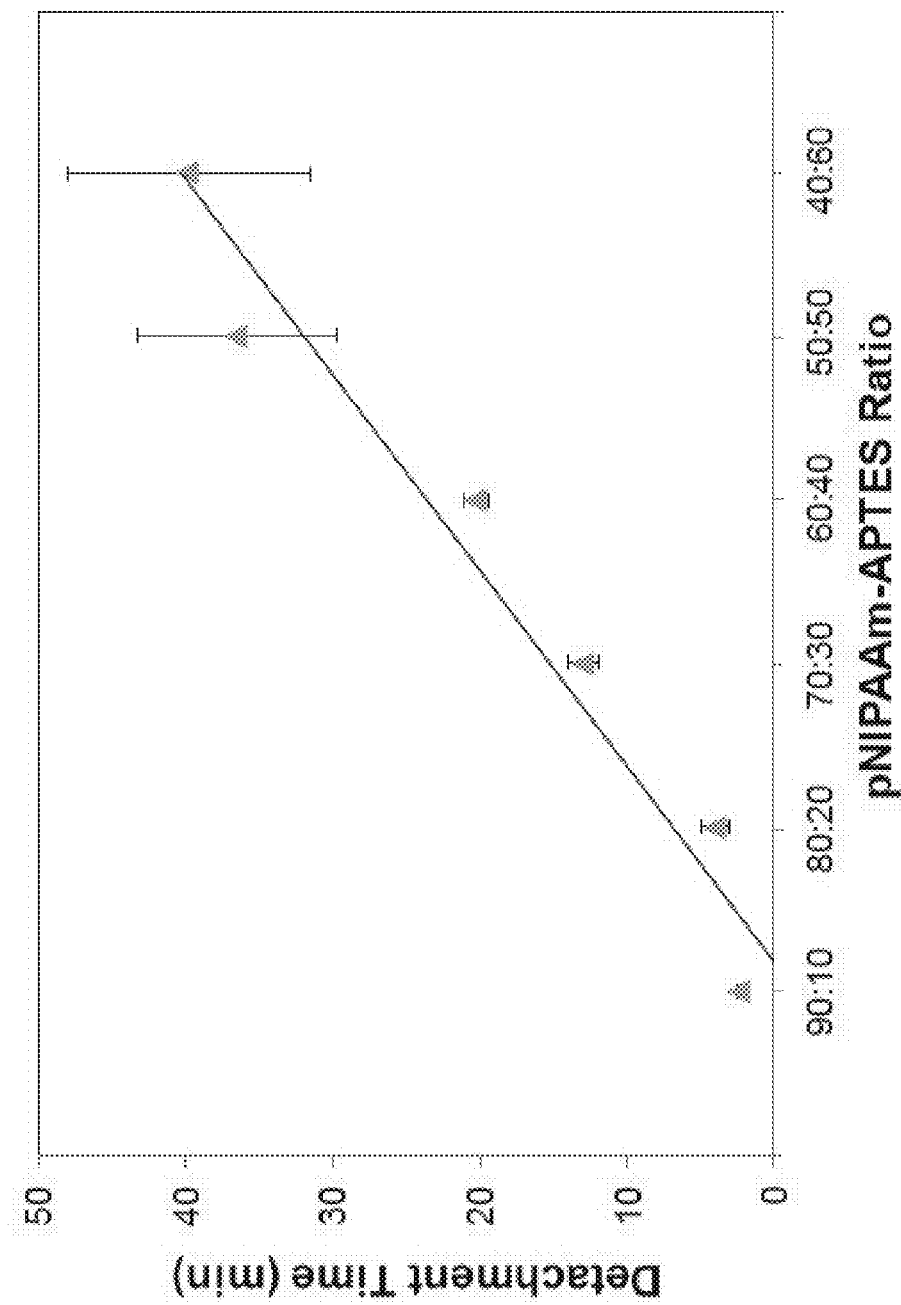
FIG. 4 shows the different cell detachment times for the surfaces with various pNIPAAm/APTES ratios.

The proposed mechanism of cell detachment is believed to be due to the extension of pNIPAAm chains burying the NH$_2$ groups of APTES, covering the anchor points needed for cell attachment. Increasing the amount of APTES in the pNIPAAm/APTES blend would lead to an increased amount of anchor points for cells. This would lead to slower cell detachment upon cooling. A simple experiment was set up to test this hypothesis by creating films of different pNIPAAm/APTES ratios, all cured at a temperature of 160° C. for 3 days. Cells were seeded on each of these films and cell detachment times for each surface were recorded. FIG. 4 shows the different cell detachment times for the surfaces with various pNIPAAm/APTES ratios. By increasing APTES, cell detachment times increased from approximately 2.5 minutes for 90:10 films to ~40 minutes for 40:60 pNIPAAm/APTES films, while the 20:80 pNIPAAm/APTES films showed no detachment.

90:10 pNIPAAm/APTES film surfaces were tested for reusable functionality. After detaching cells, surfaces were rinsed with cold media, and then reseeded with hMSCs. Cells were able to reattach and reach confluence. Once again, cold media was added over the surfaces and the cells detached as a cell sheet within 2.5 minutes. When surfaces were tested for reseeding/detachment for a third time, proper cell spreading was not observed. Instead, cell attachment was sporadic although patches of cells were still able to detach upon cooling.

Cellular Behavior on pNIPAAm Films.

pNIPAAm films produced according to the present invention provide surfaces that are biocompatible and support the maintenance of normal cellular functions. Furthermore, cell culture supports of the present invention provide cell attachment regardless of film thickness.

Cell culture supports of the present invention further provide rapid cell detachment with 4° C. medium indicating that the passive hydration of pNIPAAm chains is believed to be the main detachment mechanism as low temperature would limit the cytoskeletal action and metabolic processes to drive changes in cell morphology. Different types of mammalian cells on our surfaces have shown that cell detachment times are not affected by different cell types or by cell-cell interactions, since the detachment rates remained the same.

What is claimed is:

1. A cell culture support comprising:
   a substrate;
   a polymeric blend layer comprising at least one thermoresponsive polymer and at least one network forming adhesion promoter, characterized in that said network forming adhesion promoter is in the form of a crosslinked network bound to the substrate and said crosslinked network interlocks chains of the thermoresponsive polymer; and wherein the network forming adhesion promoter is a non-protein adhesion promoter and has functional amino or carboxylic acid groups; and
   cells supported by said polymeric blend layer, wherein said thermoresponsive polymer provides for temperature induced detachment of said cells.

2. The support of claim 1, wherein the substrate is selected from the group consisting of polymeric materials, glasses, ceramics, metals, metal oxides, hydrated metal oxides, and combinations thereof.

3. The support of claim 1, wherein the at least one thermoresponsive polymer is selected from the group consisting of poly (N-isopropylacrylamide) (PNIPAAm), poly (N,N-diethylacrylamide) (PDEAAm), poly(N-vinlycaprolactam) (PVCL), poly[2-(dimethylamino) ethyl methacrylate] (PDMAEMA), and poly(ethylene oxide) (PEO), and combinations thereof.

4. The support of claim 1, wherein the at least one thermoresponsive polymer is poly (N-isopropylacrylamide) represented by the formula:

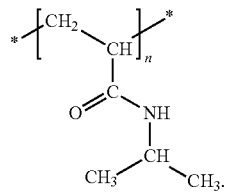

5. The support of claim 1, wherein the at least one network forming adhesion promoter is an aminosilane.

6. The support of claim 1, wherein the at least one network forming adhesion promoter is selected from the group consisting of 3-aminopropyltriethoxysilane (APTES), 3-aminopropyldiethoxymethylsilane (APDEMS), and 3-aminopropyltrimethoxysilane (APTMS), and combinations thereof.

7. The support of claim 1, wherein the at least one network forming adhesion promoter is 3-aminopropyltriethoxysilane (APTES) represented by the formula:

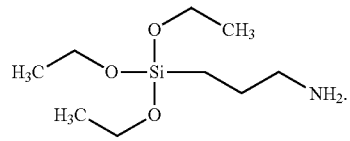

8. The support of claim 1, wherein the polymer blend layer is characterized as having a thermoresponsive polymer to network forming adhesion promoter ratio (TRP:NFAP) of from about 99:1 to about 40:60 by mass, and wherein the polymer blend layer is cured to produce a film.

9. The support of claim 1, wherein the polymeric blend layer is devoid of cell adhesive proteins.

10. The support of claim 1, wherein the polymeric blend layer is devoid of plasma or e-beam treatment.

11. The support of claim 1, wherein the support supports said cells such that said temperature induced detachment is achieved without mechanical agitation or enzymatic aided detachment methods.

* * * * *